(12) United States Patent
Katayama

(10) Patent No.: US 7,892,834 B2
(45) Date of Patent: Feb. 22, 2011

(54) CELLULAR SIGNAL-RESPONSIVE GENE TRANSCRIPTIONAL REGULATION SYSTEM

(75) Inventor: Yoshiki Katayama, Fukuoka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 618 days.

(21) Appl. No.: 10/477,735

(22) PCT Filed: Oct. 16, 2001

(86) PCT No.: PCT/JP01/09065

§ 371 (c)(1),
(2), (4) Date: Nov. 14, 2003

(87) PCT Pub. No.: WO02/095043

PCT Pub. Date: Nov. 28, 2002

(65) Prior Publication Data

US 2004/0152098 A1     Aug. 5, 2004

(30) Foreign Application Priority Data

May 17, 2001 (JP) ............... 2001-148522
Jul. 3, 2001 (JP) ............... 2001-202064

(51) Int. Cl.
| C12N 15/00 | (2006.01) |
| C12N 15/87 | (2006.01) |
| C12N 15/82 | (2006.01) |
| C12Q 1/68 | (2006.01) |
| A01N 63/00 | (2006.01) |
| A61K 38/43 | (2006.01) |
| A61K 31/74 | (2006.01) |
| A01N 43/04 | (2006.01) |

(52) U.S. Cl. .................. 435/455; 435/6; 435/320.1; 435/465; 435/468; 424/93.21; 424/94.1; 424/78.27; 514/44

(58) Field of Classification Search .................. None
See application file for complete search history.

(56) References Cited

U.S. PATENT DOCUMENTS 6,379,966 B2 * 4/2002 Monahan et al. ............ 435/455
RE39,220 E * 8/2006 Gopal ...................... 435/455

FOREIGN PATENT DOCUMENTS

WO    WO 0064486    * 11/2000

OTHER PUBLICATIONS

Lever et al., 2000, Nature 408:873-876.*
Zhang et al.,(2001, J. Biol. Chem. 276:3683-3690).*
Xu et al, 1998, Nucleic Acids Research 26:2034-2035.*
Nagai et al., 2000, Nature Biotechnology 18:313316.*
Xiao et al JBC, 272: 22191, Date: 1997.*
STIC search for SEQ ID No. 4; pp. 1-3, date: Jun. 25, 2010.*

Jose C. Perales et al., "An evaluation of receptor-mediated gene transfer using synthetic CNA-ligand complexes", Eur. Journal of Biochem. 226, 225~266 (1994).
Canadian Office Action issued on Nov. 23, 2007 in Canadian Application No. 2,447,538.
Yoshiki Katayama et al., "*Saibou-nai rinsanka shigunaru otousei idenshi seigyo shisutemu* (An Artificial Gene Regulation System Response To Protein Kinase Signal)," II Pc135, Polymer Reprints, The Society of Polymer Science, Japan, vol. 50, No. 5, p. 975 (2001).
Shigeki Sakakihara et al., "*Saibou-nai kasupaaze shigunaru otousei idenshi seigyo shrisutemu* (An Artificial Gene Regulation System Responding To Capase Signal)," II Pd136. Polymer Reprints, The Society of Polymer Science, Japan, vol. 50, No. 5, p. 975 (2001).
Yoshiki Katayama,"*Saibou jouhou to kagaku jouhou wo sougo henkan shru bunshi no sousei to kinou* (Creation of Molecules and Their Function That Covert Cell Information to Chemical Information)," 2F18, Nippon Kagakukai Chugoku Shikoku Do-Kyushu Shibu Godo Kagoshima Taikai Koen Yokoshu, vol. 2000, pp. 297-298 (2000).
Seiji Murata el al., "*Shigeki otousei porimaa/anchisensu DNA konjugeeto ni yoru idenshi hatsugen seigyo* (Preparation and characterization of stimuli-responsible antisense oligodeoxynucleotides comprising poly(*N*-isopropylacrylamide))," Polymer Reprints, The Society of Polymer Science, Japan, vol. 49, No. 13, pp. 3868-3869 (2000).
Yoshiki Katayama,"*Saibou jouhou to kagaku jouhou wo sougo henkan shru bunshi no sousei to kinou* (Creation of Molecules and Their Function That Covert Cell Information to Chemical Information)," 21st Century Chemistry and Chemical Industry, The 21st Japan Chemical Society, Kyushu Branch Symposium, pp. 15-19 (Nov. 17, 2000) (See Documents CC above and comments of Documents CF and CG below to Document CC above).
Office Action issued by Japan Patent Office mailed Nov. 27, 2007 (English translation of relevant part only is attached hereto).
English Translation of PCT/IPEA/409, Feb. 14, 2003 (7 pages).
PCT/IPEA/416 Mar. 4, 2004 (7 pages).

* cited by examiner

Primary Examiner—Robert M. Kelly
Assistant Examiner—Kelaginamane Hiriyanna
(74) Attorney, Agent, or Firm—Westerman, Hattori, Daniels & Adrian, LLP

(57) ABSTRACT

A gene complex-forming material which comprises a water-soluble polymer having a peptide containing an amino acid sequence serving as the substrate of an intracellular signal-responsive enzyme and basic amino acids imparting cationic nature; a gene complex composed of this gene complex-forming material with a gene; and a gene transfer method and a gene transfer agent with the use of the same. Namely, a novel material and a method wherein the cationic moiety of the peptide and the gene form a rigid ion complex to give a stable gene complex, and, upon a cellular signal response, the positive charge of the cationic moiety of the peptide is neutralized or disappears and the gene complex is broken in the cell to thereby release the gene, thus activating the gene transferred into specific cells. The neutralization or disappearance of the positive charge can be achieved by, for example, phosphorylation with protein kinase A or cleavage by caspase.

20 Claims, 8 Drawing Sheets

Figure 1:
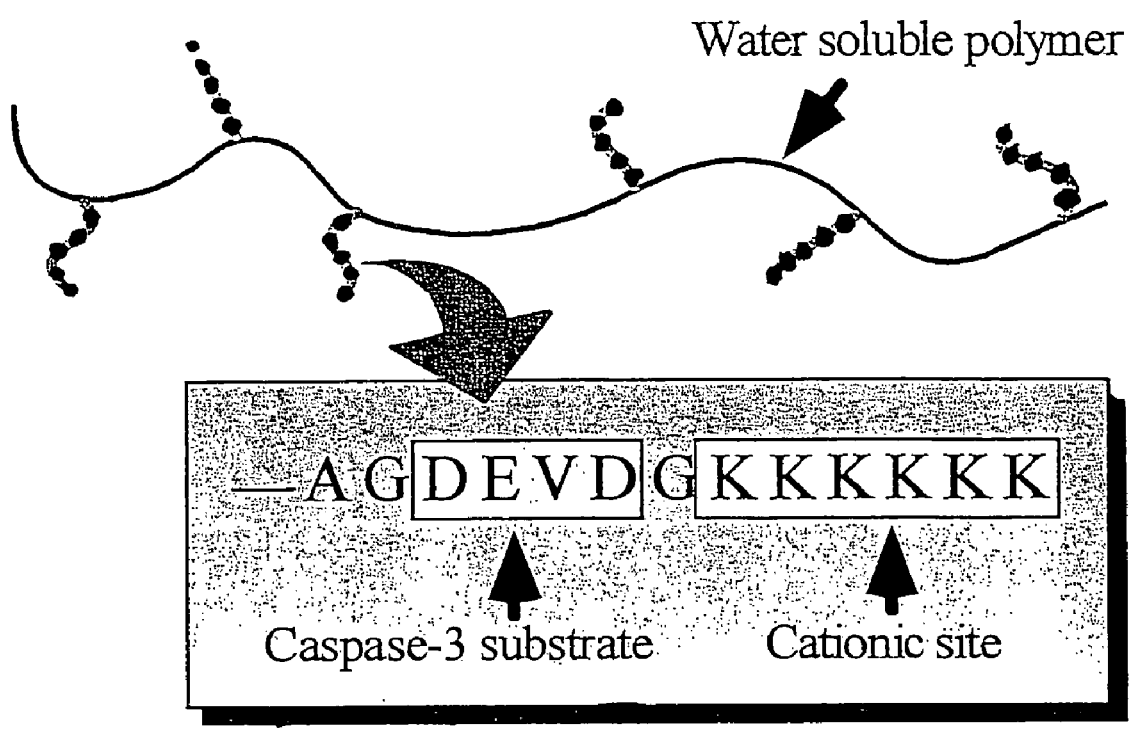

Cationic Polymer responding to the Casapase-3 Signal
(pAC polymer)

PAC polymer + PQBI63

PAC polymer + PQBI63 + caspase-3 ( 0.12U/μl)

Cation/anion
0   0.16  0.32  0.50  0.65  0.97        3.25

CELLULAR SIGNAL-RESPONSIVE GENE TRANSCRIPTIONAL REGULATION SYSTEM

TECHNICAL FIELD

The present invention relates to a gene complex-forming material which comprises a water-soluble polymer having a peptide containing an amino acid sequence serving as a substrate of an intracellular signal-responsive enzyme and a basic amino acid giving a cationic property; to a gene transfer agent; to a gene complex comprising the gene complex material and gene; and to a method for the transfer of gene using the same.

The present invention provides a novel material and method wherein the cationic moiety of the peptide and the gene form a rigid ion complex to give a stable gene complex, and, upon a cellular signal response, the positive charge of the cationic moiety of the peptide is neutralized or disappears and the gene complex is broken in the cell to thereby release the gene, thus activating the gene transferred into specific cells.

BACKGROUND OF THE INVENTION

Gene of eukaryotic cell is regularly stored in histone core which is a basic protein. Histone core is formed from four kinds of proteins called H2A, H2B, H3 and H4 and gene of about 200 bp is wound and stored in a form of a coil in one histone. The gene which is wound around the histone core is connected continuously to form a chromatin fiber (a nucleosome structure). Histone core and gene are regularly wound by an interaction on the basis of polyion complex by cationic moiety of basic protein of the histone core and anionic moiety of the gene.

The gene in such a nucleosome structure forms a stable complex with the histone core whereby the transcription is suppressed. However, as a result of bonding of the transcription factor, a histone acetyltransferase (HAT) is recruited and an amino group of lysine of a basic protein forming the histone core is acetylated whereby the positive charge of the basic protein is neutralized and the nucleosome structure of chromatin is released and disintegrated. In the gene released from the histone core, transcription becomes activated. In the structure of such a chromatin fiber, protein of the histone core having a positive charge and the gene having a negative charge form a statically stable complex and stores the gene therein. When transcription becomes necessary, the basic protein of the histone core is acetylated whereby the positive charge of the basic protein is neutralized and a static formation of complex of the histone core and the gene is disintegrated to activate the transcription.

Incidentally, in recent years, various kinds of gene therapy such as an antisense method or a gene transfer method have been developed. With regard to a method for the transfer of gene into a cell, utilization of virus, etc. has been adopted because of its efficiency but problems in terms of safety have been pointed out. For example, owing to the method, some people were dead in the Unites States. In place of above method, various methods have been developed where lipid or polymer having positive charge is subjected to a static interaction with gene having negative charge and the resulting complex is transferred into the cell.

In those methods however, it is necessary to make the complex more stable to increase the efficiency of transfer into the cell while, on the other hand, transcription of gene is suppressed when it remains complex. Therefore, in order to increase the efficiency of the gene expression transferred into the cell, it is necessary to satisfy the contradictory condition such that the complex transferred into the cell is quickly disintegrated to be in a state of a transferable gene. Consequently, the efficiency of gene transfer in the already-known methods is quite low.

Accordingly, there has been a demand for the development of a complex in which, in a normal state, a stable complex is formed and the gene is stably held there and, in a state where activation of the gene is necessary, the complex is quickly disintegrated and the gene is released therefrom.

DISCLOSURE OF THE INVENTION

The present invention aims to provide a complex in which, in a normal state, a stable complex is formed and the gene is stably held there and, in a state where activation of the gene is necessary, the complex is quickly disintegrated and the gene is released to provide a material for such a complex.

Further, the present invention aims to provide a gene complex which is able to be specifically disintegrated by an action of a specific enzyme and also to provide a material for the complex.

Furthermore, the present invention aims to provide a gene transfer agent in gene therapy.

BRIEF DESCRIPTION THE DRAWINGS

FIG. 1 schematically shows an outline of interaction by between a caspase-3 signal in the gene complex-forming material of the present invention, in an embodiment that includes SEQ ID NO: 1.

Figure 2:
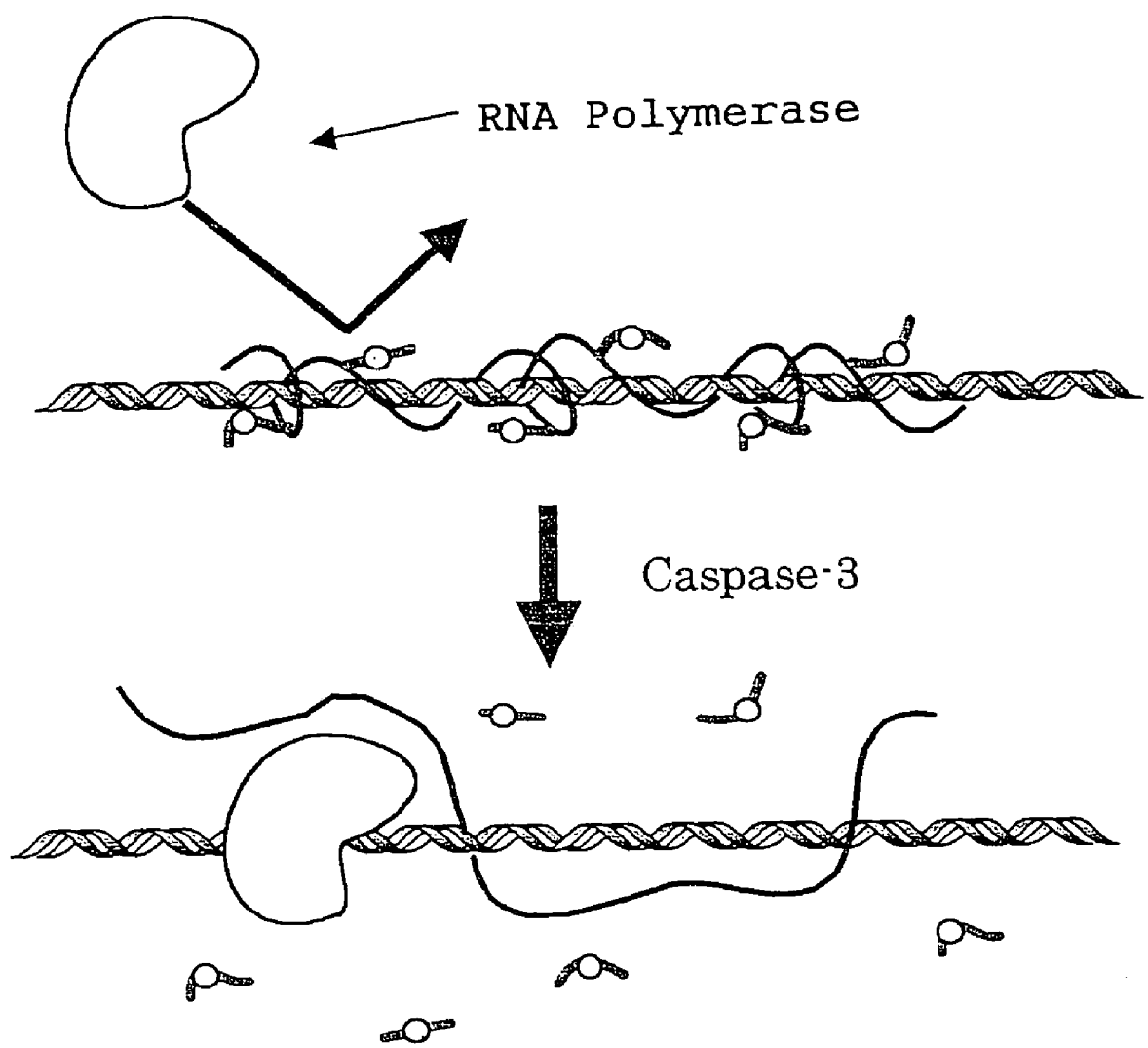

FIG. 2 schematically shows an outline of RNA polymerase and interaction by a caspase-3 signal in the gene complex-forming material of the present invention.

Figure 3:
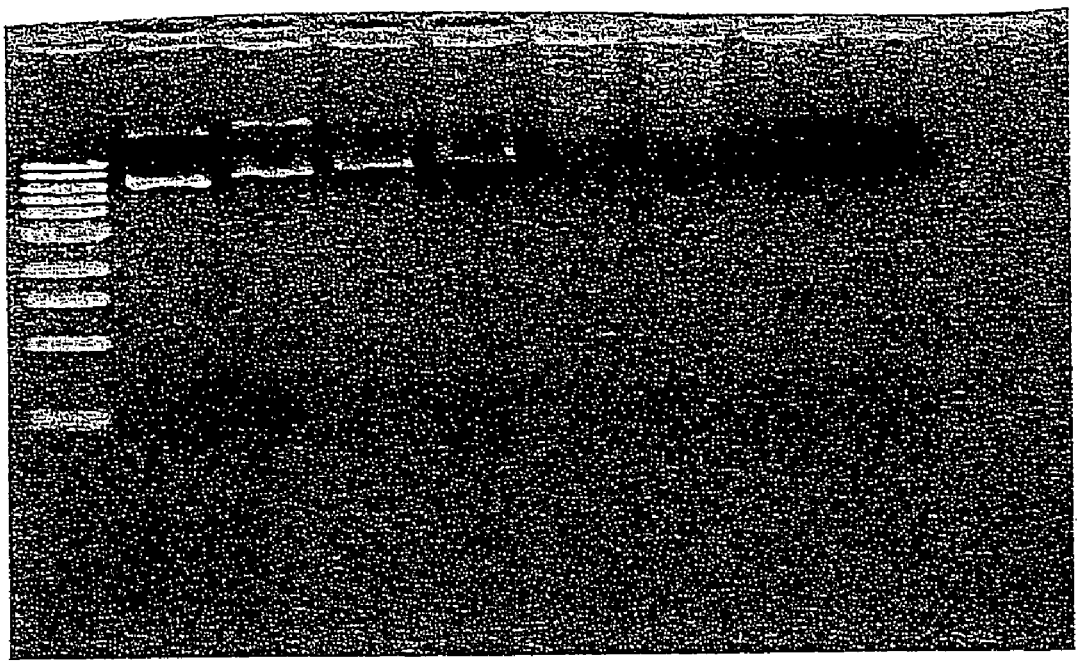

FIG. 3 is a photo substituted for a drawing showing the result of gel electrophoresis conducted under various ratios of cation/anion after mixing a plasmid DNA (pQBI 63) with a pAC polymer of the present invention. The most left side lane of FIG. 3 is a 1 kb DNA marker; the next lane thereof is pladmid DNA (pQBI 63) (ratio of cation:anion=0); the other lanes are the lanes where the cation:anion ratio is 0.5 (the third lane from the left side), 1.0 (the fourth lane from the left side), 1.5 (the fifth lane from the left side), 2.0 (the sixth lane from the left side) and 3.0 (the seventh lane from the left side), successively; and the ratio is 10.0 (the ninth lane from the left-hand side).

Figure 4:
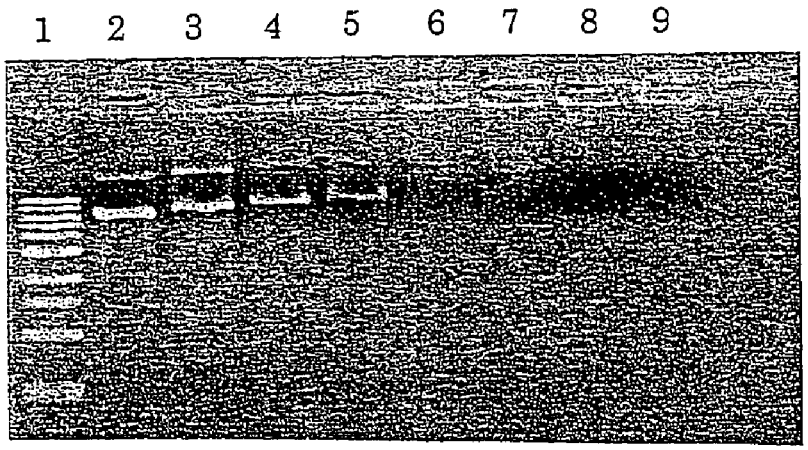
Figure 4:
Figure 4:

FIG. 4 is photo substituted for a drawing showing the results of gel electrophoresis conducted before and after the treatment of the pAC polymer of the present invention and the plasmid DNA (pQBI 63) with caspase-3 under various ratios of cation/anion. The upper picture of FIG. 4 is a result before the treatment with caspase-3 while the lower picture is that after the treatment. Lane 1 of FIG. 4 is 1 kb DNA marker; lane 2 is plasmid DNA (pQBI 63) (ratio of cation:anion=0); lanes 3 to 8 are those where the ratios of cation:anion are 0.5 (lane 3), 1.0 (lane 4), 2.0 (lane 5), 3.0 (lane 6), 5.0 (lane 7) and 10.0 (lane 8) successively.

Figure 5:
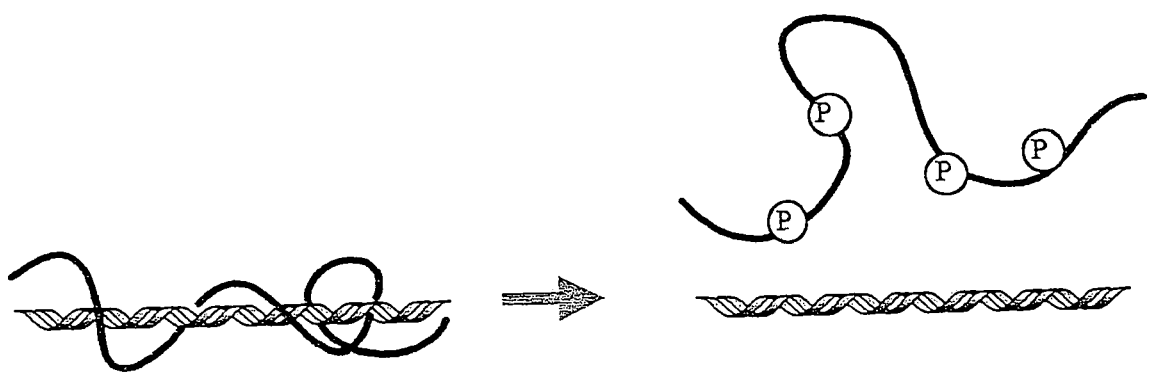

FIG. 5 schematically shows an outline of interaction by a phosphorylation signal of the present invention.

Figure 6:
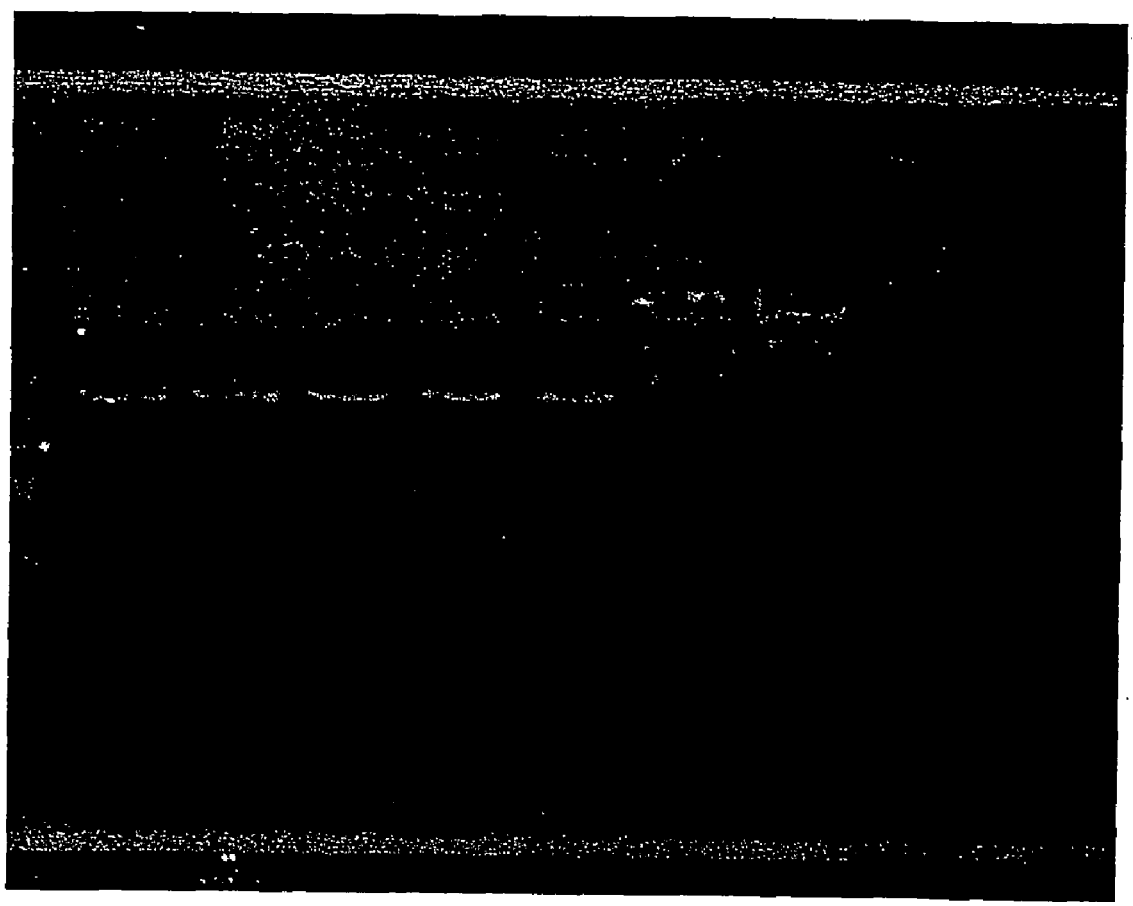

FIG. 6 is a photo substituted for a drawing showing the result of gel electrophoresis conducted under various ratios of cation/anion after mixing a plasmid DNA (pET 16b) with a pAK polymer of the present invention. The most left side lane of FIG. 6 is plasmid DNA (pET 16b) (ratio of cation:anion=0) and the other lanes are the lanes where the cation:anion ratio is 0.16 (the second lane from the left side), 0.32 (the third lane from the left side), 0.5 (the fourth lane from the left side), 0.65

(the fifth lane from the left side) and 0.97 (the sixth lane from the left side), successively; and the ratio is 3.25 (the eighth lane from the left side).

Figure 7:
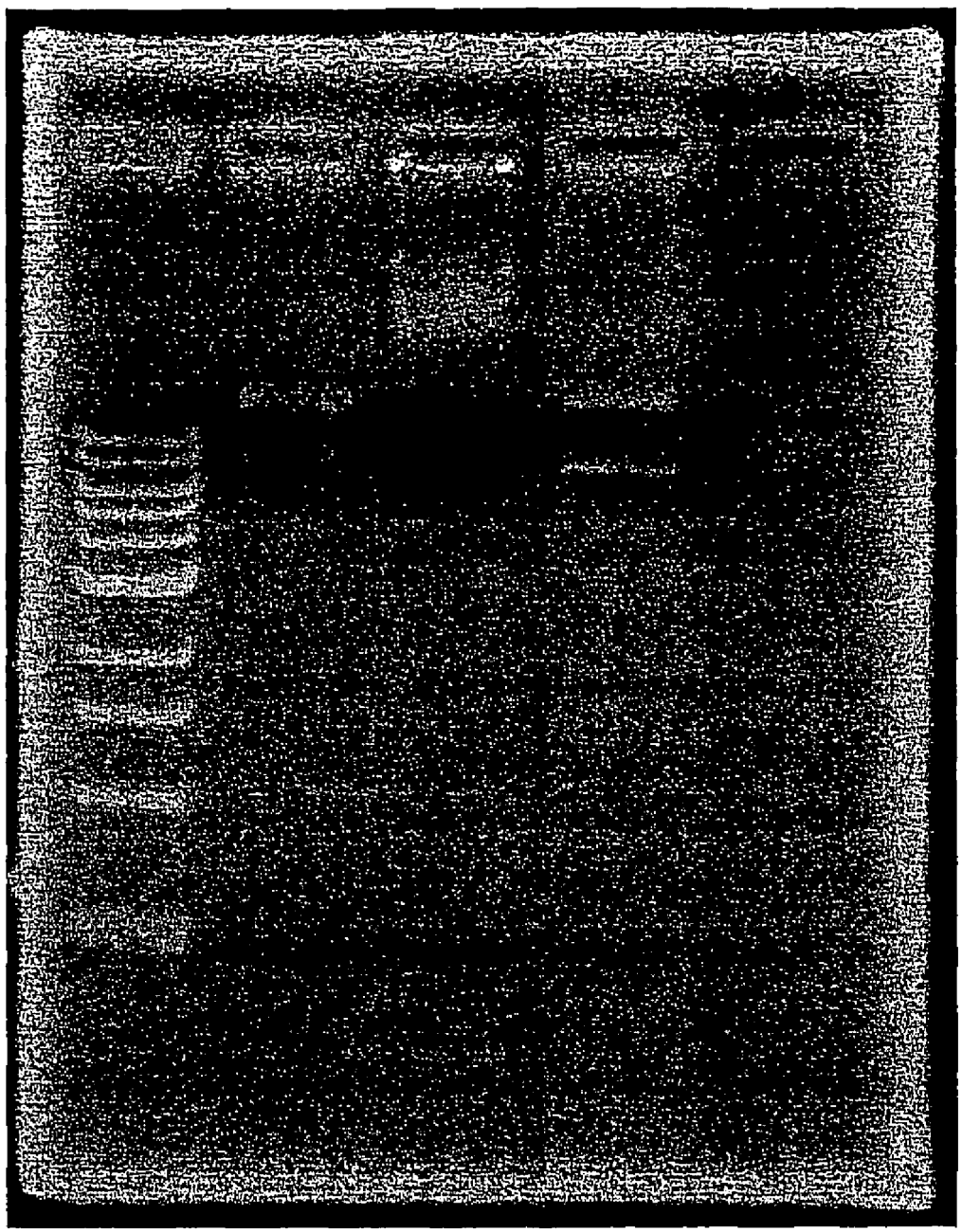

FIG. 7 is a photo substituted for a drawing showing the result of gel electrophoresis conducted before and after the treatment with protein kinase A when the ratio of cation/anion is 3.2. Lane 1 of FIG. 7 is 1 kb DNA marker; lane 2 is plasmid DNA (pET 16b); lane 3 is a complex of the plasmid DNA (pET 16b) with a pAK polymer; and lane 4 is the case after treating the complex of the lane 3 with protein kinase A.

Figure 8:
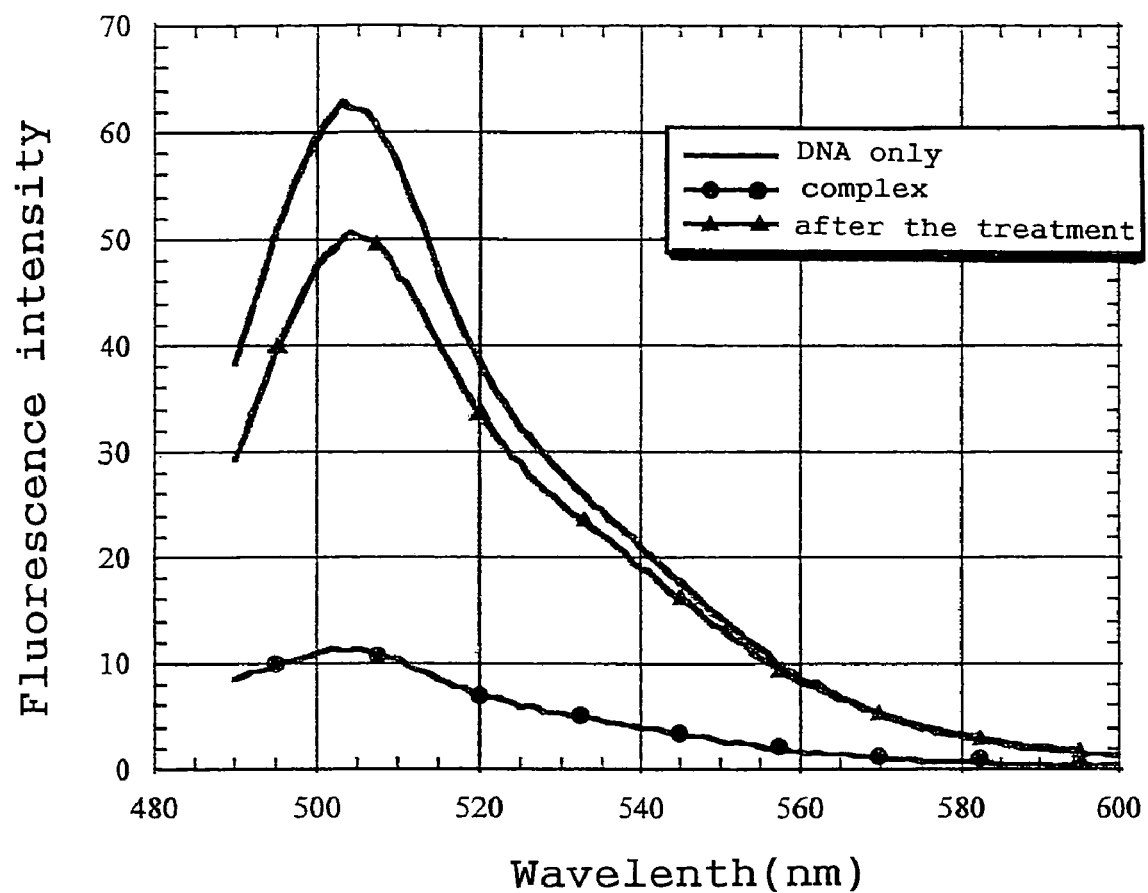

FIG. 8 shows the result of measuring the GFP fluorescence expressed for each of gene (pQBI 63), gene-pAK protein complex and a solution in which active protein kinase A is added to the complex to phosphorylate. The ordinate of FIG. 8 shows fluorescence intensity while an abscissa shows wavelength (nm). In FIG. 8, a solid line shows fluorescence of GFP expressed from the gene (pQBI 63), a line with black dots (●) shows fluorescence of GFP expressed from the gene-pAK protein complex, and a line with black triangles (▲) shows fluorescence of GFP expressed from the phosphorylated complex.

BEST MODE FOR CARRYING OUT THE INVENTION

In a nucleosome structure of natural gene, transcription of gene is activated by acetylation of a basic amino acid, and using it as a model, the present inventor has investigated the activation of gene applying an intracellular signal response of cells. Thus, it has been investigated that although cationic polymer and gene forms a strong polyion complex by a charge interaction, anionic group is introduced into the cationic polymer or cationic moiety is cleaved to neutralize or remove the positive charge of the polymer chain so that a charge interaction between the cationic polymer and the gene is attenuated whereby transcription of the gene is activated.

The present inventor has now investigated utilization of the intracellular signal response as a method for the introduction of anionic group into the cationic polymer or as a method for the removal of the cationic moiety.

Thus, the present invention relates to a gene complex-forming material which comprises a water-soluble polymer having a peptide containing an amino acid sequence serving as the substrate of an intracellular signal-responsive enzyme and a basic amino acid giving a cationic property; to a gene transfer agent; to a gene complex comprising the gene complex material and gene; and to a gene transfer method using the same.

The system of the present invention shows a completely new concept that abnormal signal in a cell is perceived whereby transcription and expression of the gene are activated. Namely, even if a stable complex which is necessary for cell transfer is formed, the complex is able to be positively disintegrated in the cell responding to the signal only in a cell giving a certain type of signal and expression of the transferred gene becomes possible only in the target cell giving an abnormal signal.

By using the concept, a really cell-selective gene therapy which has been impossible becomes possible. Namely, it is possible for the gene of the therapy to work only in the abnormal cell in the tissue. Until now, there has not existed the way of thinking that a signal in a cell is perceived and responded to control the expression of transgene.

An intracellular signal response used in the present invention is a protein phosphorylation signal, a protease signal or the like in a signal transduction system of cells.

In the following explanation, as an example of the intracellular signal response of the present invention, a caspase-3 signal among caspase (enzyme) signals which are important in signal transduction for cell death which is a kind of protease signals is used to explain specifically. The protease signal is an intracellular signal which decomposes protein and plays an important role in various intracellular transduction of information.

In caspase-3, an amino acid sequence of -DEVD- (-Asp-Glu-Val-Asp-) is a substrate thereof. Lysine was used as a basic amino acid which gives cationic property to the amino acid sequence. As a peptide containing a basic amino acid giving cationic property and amino acid sequence which is a substrate for a phosphorylation signal response, a peptide having an amino acid sequence of

SEQ ID NO: 1
-AGDEVDGKKKKKK- (-Ala-Gly-Asp-Glu-Val-Asp-Gly-Lys-Lys-Lsy-Lsy-Lsy-)

was prepared.

As a polymer skeleton of a water-soluble polymer, a copolymer of acrylic acid-methacrylic acid was used. Namely, a gene complex-forming material of the present invention was prepared by copolymerization of N-methacryloyl-peptide and acrylamide. Outline of the synthetic method is shown by chemical formulae represented by the following synthetic method (I).

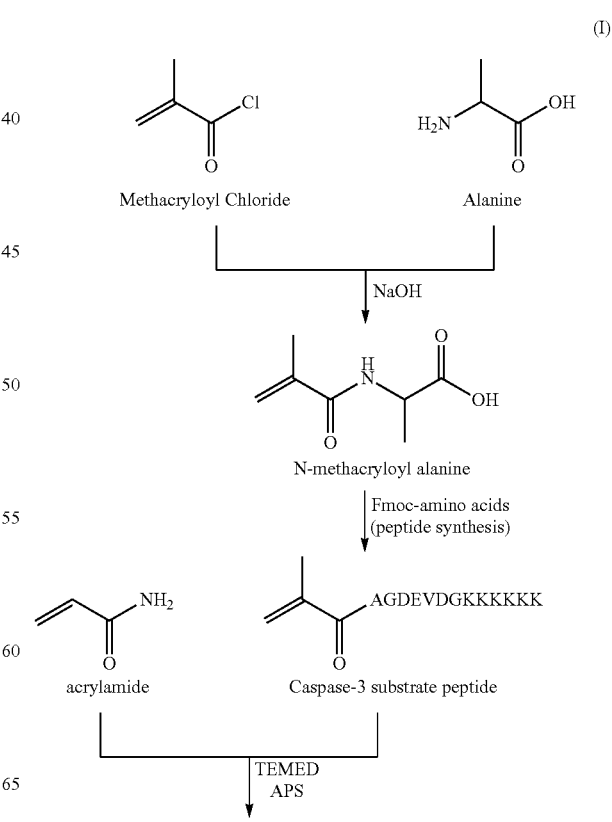
(I)

-continued

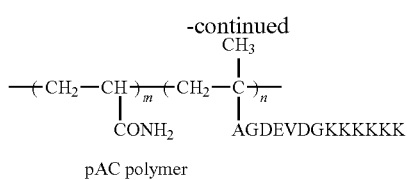

pAC polymer

A schematic chart of the resulting gene complex-forming material of the present invention is shown in FIG. 1.

A peptide containing a basic amino acid giving cationic property and an amino acid sequence which is a substrate for the above-mentioned protease of the present invention (in FIG. 1, it is shown by a line with black dots) is hung down from a skeleton of a water-soluble polymer comprising an acrylic acid-methacrylic acid copolymer. An amino acid sequence of the peptide has a moiety which is a substrate for caspase-3 (the left side moiety surrounded by a square in the lower part of FIG. 1) and a basic amino acid giving a cationic property (the right side moiety surrounded by a square in the lower part of FIG. 1). Alanine and glycine which are not surrounded by a square in FIG. 1 play roles of linkers used for bonding the above-mentioned moieties.

Outline of function of a caspase-3 signal-responsive cationic polymer (hereinafter, referred to as pAC polymer) as shown in FIG. 1 is shown in FIG. 2. A state where the gene (in FIG. 2, it is shown by ribbon double strands) and the pAC polymer form a complex, is shown in the upper part of FIG. 2. In such a state, the pAC polymer and the gene form a strong polyion complex by a charge interaction. Therefore, even an RNA polymerase comes near in this state, the RNA polymerase cannot work along the gene and transcription is not possible.

If caspase-3 is activated via a signal transduction system in the state, the caspase-3 recognizes the substrate part in the pAC polymer and selectively cleaves the peptide at that part. As a result, the cationic part of the pAC polymer is lost whereby a charge interaction with the gene is unable to be maintained and a complex of the gene with the pAC polymer is disintegrated. As a result, the gene is released and a transcription by an RNA polymerase becomes possible.

Next, an interaction of the polymer with the gene was investigated.

As a gene, a plasmid DNA (pQBI 63) coding GFP (green fluorescent protein) emitting green fluorescence was used. The pAC polymer containing 0.9 mol % of the above peptide was mixed with the plasmid DNA (pQBI 63) and subjected to gel electrophoresis in various ratios of cation/anion. The result is shown in FIG. 3 by a photo substituted for a drawing. The most left side lane of FIG. 3 is a 1 kb DNA marker; the next lane thereof is plasmid DNA (pQBI 63) (ratio of cation:anion=0); the other lanes are the lanes where the cation:anion ratio is 0.5 (the third lane from the left side), 1.0 (the fourth lane from the left side), 1.5 (the fifth lane from the left side), 2.0 (the sixth lane from the left side) and 3.0 (the seventh lane from the left-side), successively; and the ratio is 10.0 (the ninth lane from the left side). The condition for the gel electrophoresis was 50 minutes at 100 V using agarose (0.1 g/10 ml) in 100 mM TBE buffer (pH 7.4).

In the second lane from the left side in FIG. 3 (gene only), two bands of gene can be clearly observed but, as the ratio of cation becomes higher (amount of pAC polymer becomes more), the band of the gene becomes thinner and, it is noted that when the ratio of cation:anion becomes 10.0, the band of the gene completely disappears. It means the gene forms a strong complex by a charge interaction with the pAC polymer whereby it is unable to move on the gel.

Next, the action by caspase-3 was investigated.

In various ratios of cation/anion, gel electrophoresis was conducted before and after the treatment with caspase-3. The result is shown in FIG. 4 by a photo substituted for a drawing. The upper picture of FIG. 4 is the result before the treatment with caspase-3 while the lower picture is that after the treatment with caspase-3. Lane 1 of FIG. 4 is 1 kb DNA marker; lane 2 is plasmid DNA (pQBI 63) (ratio of cation:anion=0); lanes 3 to 8 are those where the ratios of cation:anion are 0.5 (lane 3), 1.0 (lane 4), 2.0 (lane 5), 3.0 (lane 6), 5.0 (lane 7) and 10.0 (lane 8) successively. The condition for the gel electrophoresis was 40 minutes at 100 V using agarose (0.1 g/10 ml) in 100 mM TBE buffer (pH 7.4).

Before the treatment, as shown in the upper picture of FIG. 4, band of the gene in lanes 6 to 8 is unable to be observed as same in the case of FIG. 3, howeber, after the treatment with caspase-3 (0.12 U/μl), as shown in the lower picture, the band of the gene is able to be observed. It shows that the gene forms a strong complex by a charge interaction with the pAC polymer whereby it is unable to move on the gel and, as a result of the treatment with caspase-3, the complex is disintegrated and the gene is released.

In this example, a method using a protease signal has been shown. A polymer used in this example is a water-soluble polymer where polyacrylamide carrying a peptide (AGDEVDGKKKKKK) having a positive charge is a basic structure and, between the positively charged part of the transferred peptide and the polymer main chain, a peptide sequence which is selectively cleaved by caspase-3 is integrated. When the polymer is mixed with the gene, a complex is formed by a static interaction and gene transcription is suppressed. However, when the peptide of the polymer in the complex is cleaved by caspase-3, a positively charged part is removed from the polymer chain. Further, since it is designed for negative charges in the residual polymer part, repulsion of negative charges take place in the complex whereby the complex is disintegrated and the gene is released.

In this example, caspase-3 is used as a protease signal although it is non limited to this and, when a peptide sequence is used as a substrate sequence for a target protease, it is principally applicable to any protease.

In this example, although a copolymer of acrylic acid with methacrylic acid is used as a water-soluble polymer, any polymer may be used principally so far as it is a water-soluble polymer. Abnormality of a protease signal is also noted in hepatitis, in various inflammatory diseases and in many neurodegenerative diseases such as Alzheimer's disease and the system where a signal is captured to activate a transferred gene has a very high utility value.

Next, an example where a phosphorylation signal response system is utilized is shown.

A phosphorylation signal is on the basis of the activation of various kinds of intracellular kinases (enzymes) and it is a system in which a target protein is phosphorylated whereby activity of the protein is changed to transmit the signal in the cell. It is the most basic and frequently used signal in an intracellular information transmittance system. Although here is exemplified a system which responds to a signal of protein kinase A which is a basic and important kinase, an entirely same system is also applicable to other kinase by using a substrate sequence corresponding to other kinase and the present system is not limited to protein kinase A.

To be more specific, a water-soluble polymer, in which polyacrylamide having a positive charge and carrying a substrate peptide (ALRRASLG-NH$_2$) which is selectively phosphorylated by protein kinase A is a basic skeleton, is developed. Since this polymer has many positive charges in a molecule, it forms a complex by a static interaction when mixed with gene. As a result, protein which is necessary for transcription of gene is unable to come closer and transcription expression of the gene is suppressed. However, when a substrate peptide in this complex is phosphorylated by protein kinase A, a phosphate anion is introduced into the polymer to attenuate a static interaction between the gene and the polymer. Therefore, the gene is released from the complex, transcription of the gene becomes possible and activation is achieved. As a polymer chain, polyacrylamide is a basic skeleton here but, principally, anything may be utilized so far as it is a water-soluble neutral polymer. Activity abnormality of kinase forming a phosphorylation signal has been known in various cancers and cardiac diseases and, when gene expression control is possible by perceiving such an abnormal signal, it becomes possible to create an entirely novel pharmaceutical concept.

Arginine was used as a basic amino acid for giving a cationic property to amino acid sequence and a peptide having an amino acid sequence of

SEQ ID NO: 3
-ALRRASLG-NH$_2$ (-Ala-Leu-Arg-Arg-Ala-Ser-Leu-Gly-NH$_2$)

was prepared as a peptide containing a basic amino acid giving cationic property and amino acid sequence which is to be a substrate for a phosphorylation enzyme.

As a polymer skeleton of a water-soluble polymer, a copolymer of acrylic acid with methacrylic acid was used as same as mentioned above. Thus, in the N-terminal of the above-mentioned peptide, methacrylic acid was amidated and copolymerized with acrylic acid amide to prepare a gene complex-forming material of the present invention. Outline of a synthetic method thereof is shown by chemical formulae as shown by the following synthetic method (II).

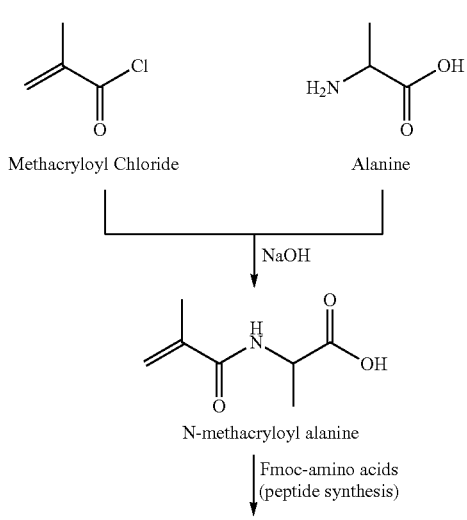

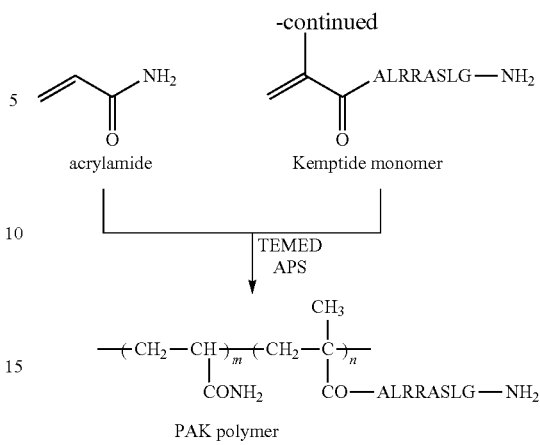

Outline of function of a protein kinase A signal-responsive cationic polymer (hereinafter, referred to as pAK polymer) is shown in FIG. 5. A state where the gene (in FIG. 5, it is shown by ribbon double strands) and the pAK polymer form a complex is shown in the left side of FIG. 5. In such a state, the pAK polymer and the gene form a strong polyion complex by a charge interaction. Therefore, even an RNA polymerase comes near in such a state, the RNA polymerase is unable to work along the gene and transcription is not possible.

If protein kinase A is activated via a signal transduction system in such a state, the protein kinase A recognizes the substrate part in the pAK polymer and it is phosphorylated. As a result, the cationic part of the pAK polymer is lost whereby a charge interaction with the gene is unable to be maintained and a complex of the gene with the pAK polymer is disintegrated. As a result, the gene is released and a transcription by an RNA polymerase becomes possible.

Next, an interaction of the polymer with the gene was investigated.

As a gene, a plasmid DNA (pET 16b) coding GFP (green fluorescent protein) emitting green fluorescence was used as same as mentioned above. The pAK polymer containing 0.9 mol % of the above peptide was mixed with the plasmid DNA (pET 16b) and subjected to gel electrophoresis in various ratios of cation/anion. The result is shown in FIG. 6 by a photo substituted for a drawing. The most left side lane of FIG. 6 is plasmid DNA (pET 16b) (ratio of cation:anion=0) and the other lanes are the lanes where the cation:anion ratio is 0.16 (the second lane from the left side), 0.32 (the third lane from the left side), 0.5 (the fourth lane from the left side), 0.65 (the fifth lane from the left side) and 0.97 (the sixth lane from the left side), successively; and the ratio is 3.25 (the eighth lane from the left side). The condition for the gel electrophoresis was 50 minutes at 100 V using agarose (0.1 g/10 ml) in 100 mM TBE buffer (pH 7.4).

In the first lane from the left side in FIG. 6 (gene only), two bands of gene can be clearly observed but, as the ratio of cation becomes higher (amount of pAK polymer becomes more), band of the gene becomes thinner and, it is noted that when the ratio of cation:anion becomes 3.25, the band of the gene completely disappears. It means the gene forms a strong complex by a charge interaction with the pAK polymer whereby it is unable to move on the gel.

Next, an action by protein kinase A was investigated.

Gel electrophoresis was carried out before and after the treatment with protein kinase A for the case where the ratio of cation/anion is 3.2. The result is shown in FIG. 7 by a photo substituted for a drawing. In FIG. 7, lane 1 is 1 kb DNA marker; lane 2 is a plasmid DNA (pET 16b); lane 3 is a complex of a plasmid DNA (pET 16b) with a pAK polymer; and lane 4 is the case after the complex of the lane 3 is treated with protein kinase A. The condition for the gel electrophoresis was 100 V for 40 minutes using agarose (0.1 g/10 ml) in 100 mM TBE buffer (pH 7.4).

In the lane 2 (gene only) of FIG. 7, two bands of gene are observed, however, when a pAK polymer is added thereto to form a complex, the gene bands disappears (lane 3). When it is subjected to a phosphorylation treatment with protein kinase A, the gene bands are able to be observed again (lane 4).

It shows, the gene forms a strong complex by a charge interaction with the pAK polymer whereby it is unable to move on the gel. However, when a treatment with protein kinase A is conducted, the complex is disintegrated and the gene is released.

Next, a transcription activated experiment by a protein kinase A signal using a complex was carried out.

GFP was expressed for each of the gene (pQBI 63), a gene-pAK protein complex and a solution where the complex is phosphorylated with active protein kinase A and the fluorescence was measured. The result is shown in FIG. 8. An ordinate of FIG. 8 shows fluorescence intensity while an abscissa shows wavelength (nm). In FIG. 8, a solid line shows fluorescence of GFP expressed from the gene (pQBI 63), a line with black dots (●) shows fluorescence of GFP expressed from a gene-pAK protein complex and a line with black triangles (▲) shows fluorescence of GFP expressed from the phosphorylated complex.

As being apparent from the result of FIG. 8, although GFP expressed from the gene (pQBI 63) shows a strong fluorescence intensity around 505 nm, such characteristic fluorescence disappears when it forms a complex with pAK polymer of the present invention (a line with black dots (●) in FIG. 8). When the complex is treated with protein kinase A and the peptide moiety is phosphorylated (a line with black triangles (▲) in FIG. 8), fluorescence of nearly the same intensity is able to be observed at nearly the same position as in the case of GFP obtained from the original gene, whereby it is noted that the gene is released from the complex by the phosphorylation and transcription is activated.

As mentioned hereinabove, the present invention is on the basis of a completely new concept that abnormal signal in a cell is perceived whereby transcription and expression of the gene are activated. Thus, for example, even if a stable complex which is necessary for cell transfer is formed at the time of the transfer of gene into the cell, the complex is able to be positively disintegrated in the cell responding to the signal only in the cell giving a certain type of signal and expression of the transferred gene selectively activated in the target cell giving an abnormal signal.

The present invention provides a gene complex-forming material which comprises a water-soluble polymer having a peptide containing an amino acid sequence serving as a substrate of an intracellular signal-responsive enzyme and a basic amino acid giving a cationic property; a gene transfer agent; a gene complex comprising the gene complex material and gene; and a gene transfer method using the same.

The enzyme used in the present invention may be any enzyme so far as it relates to a signal transduction system and a signal response system in a cell and is an enzyme relating to protein phosphorylation signal, protease signal, etc. Preferably, it is an enzyme participating in a signal response specifically acting on the type of cell such as tumor cell. In the above-mentioned examples, it has been mentioned for the case where caspase-3 is used as an example of protease signal and protein kinase A is used as an example of phosphorylation signal. However, with regard to the enzyme of the present invention, any enzyme may be used principally where the used peptide sequence is made into a substrate sequence of the target enzyme. Therefore, it is not limited to the above-exemplified enzymes.

The peptide of the present invention contains an amino acid sequence which is to be a substrate for the enzyme of the intracellular signal response and a basic amino acid giving a cationic property and, in addition, it may also contain an amino acid sequence which is to be a substrate for the enzyme of the phosphorylation signal response, an amino acid sequence which is a linker for bonding a part comprising a basic amino acid giving a cationic property and a sequence which is a linker for bonding to a skeleton of the water-soluble polymer. There is no particular limitation for the length of the peptide of the present invention and, although it may be considerably long, it is preferred to be about 10 to 50 amino acids, 10 to 30 amino acid or 10 to 20 amino acids when easiness in the manufacture is taken into consideration.

With regard to an amino acid sequence which is to be a substrate for the enzyme of intracellular signal response of peptide of the present invention, it is preferable to be selectively recognized by a target enzyme and is either phosphorylated or cleaved at or near the recognized site. It is acceptable if a cationic property of the site giving a cationic property to the peptide is neutralized by the action of the target enzyme, or if a cationic property of the cationic peptide is lost as a result of separation by cleavage of the site.

With regard to the site containing a basic amino acid giving a cationic property of the peptide of the present invention, anything may be used so far as it contains at least one, preferably two or more, basic amino acid such as lysine, arginine and histidine. It is possible to adjust the cationic property of the peptide of the present invention depending upon the gene which is to be subjected to an interaction.

With regard to the skeleton of the polymer of the present invention, there is no particular limitation so far as it is a water-soluble polymer and, although it is preferable to have no particular physiological activity in living body, it is recommended to have a bioaffinity. Since the above-mentioned peptide of the present invention is bonded to the skeleton of the polymer, it is preferable to have a functional group which is able to bond to a peptide. In the already-mentioned examples, polymers of acrylic acid and methacrylic acid systems are exemplified but they are not limited.

There is also no particular limitation for size and molecular weight of the polymer of the present invention and they may be appropriately decided in view of length of the gene used, affinity of to cells, etc. The polymer of the present invention may be either copolymer, homopolymer or block polymer and there is no particular limitation therefor.

The polymer of the present invention is acceptable so far as it is soluble in water and has a bioaffinity and, in case where a peptide is carried on an insoluble substance, a monomer which is able to form a water-soluble polymer is used whereby it is also possible to give a water-soluble polymer as a polymer.

The gene complex-forming material of the present invention comprises the above-mentioned peptide-bonded water-soluble polymer of the present invention and, with regard to a process for producing the same, already-known methods may be adopted. In the above-mentioned producing example, an example where peptide is bonded to a methacrylic acid monomer and the resulting monomer is polymerized is shown, however, it is not limited to the method. A peptide moiety may be separately produced and a monomer is modified followed by polymerizing or a water-soluble polymer may be modified using a separately produced peptide.

The gene of the present invention may be anything so far as it is anionic and, although both DNA and RNA is acceptable, DNA is usually preferred. Length of the gene may be optional provided that it is neither extremely long nor extremely short but, usually, that of about 10 to 5000 bases or 20 to 2000 bases is preferable. It is also possible to adjust the length of the polymer depending upon the length of the gene used. It is further possible that, depending upon the charge of the gene used, amount of the gene complex-forming material of the present invention is adjusted or the cationic charge amount of the gene complex-forming material of the present invention is adjusted.

The gene complex-forming material of the present invention having a cationic peptide moiety can be used as a stable gene complex by forming a strong ion complex with the gene. The gene complex specifically loses its cationic property by the action of the enzyme corresponding to the specific signal response in a cell to be disintegrated and release the gene. Accordingly, the gene complex-forming material of the present invention is able to be used as a gene transfer agent for a living body and the present invention provides a method for the transfer of gene using a gene complex comprising the gene complex-forming material and gene.

The transferred gene may be either antisense or gene which expresses a specific protein. According to the method of the present invention, if a gene complex is non specifically transferred to the cell, the gene is released from the gene complex specifically only in the cell where a signal response is available and, as a result, there is provided a method where gene is transferred in a cell-specific manner.

The present invention is able to specifically react depending upon a signal response of the cell and, therefore, it can be utilized for the treatment and prevention of various diseases caused by signal response.

For example, abnormality of protease signal is observed in hepatitis, various inflammatory diseases and many neurodegenerative diseases such as Alzheimer's disease and the system where a signal is captured to activate a transferred gene has a very high utility value. In addition, abnormality of activity of kinase forming a phosphorylation signal has been known in various cancers and cardiac diseases and, when such an abnormal signal is perceived and gene expression is able to be controlled, it becomes possible to create an entirely novel pharmaceutical concept.

The present invention will now be illustrated in more details by way of the following Examples although the present invention is not limited thereto.

EXAMPLES

Example 1

Synthesis of Protease Signal-Responsive Polymer

It was produced by the above-mentioned synthetic method (I). Namely, a monomer of a substrate peptide type was synthesized and then it was subjected to a radical copolymerization with acrylamide to give an aimed product. With regard to the monomer of a substrate peptide type, N-methacryloylalanine was synthesized and then it and other Fmoc amino acid were used to synthesize the monomer by means of a solid phase synthesis using an automatic peptide synthesizer.

(1) Synthesis of N-Methacryloylalanine

Sodium hydroxide (1.24 g) and L-alanine (2.76 g) were dissolved in pure water and, under cooling with ice, a solution where methacryloyl chloride (3 ml) was dissolved in THF (15 ml) and an aqueous solution (17 ml) containing sodium hydroxide (1.21 g) were simultaneously dropped thereinto. After that, the mixture was stirred at room temperature for 4 hours, acidified with 2M hydrochloric acid and extracted with ethyl acetate. The organic phase was dried, concentrated in vacuo, washed with ether and dried in vacuo to give the aimed product. Yield: 1.76 g (36%).

(2) Synthesis of Monomer of a Peptide Type

Each Fmoc-amino acid (0.8 mmol) was weighed in a reactor and a peptide was synthesized by an automatic synthesizer. After the reaction, a peptide resin was added to a mixed solution of trifluoroacetic acid (9.5 ml), pure water (0.25 ml) and triisopropylsilane (0.25 ml) and the mixture was allowed to stand for 2 hours and sucked. The resin was washed with trifluoroacetic acid, the washing and the filtrate were combined, ether in a ten-fold amount was added thereto and the peptide separated out therefrom was filtered and dried in vacuo. The crude peptide was purified by a reverse phase HPLC (0.1% aqueous solution of TFA/0.1% TFA-acetonitrile=15%→50% (15 minutes)) whereby 36 mg of monomer of a peptide type were prepared.

(3) Synthesis of a Polymer

Acrylamide (14 mg) and 25 mg of the monomer of a peptide type prepared in the above (2) were dissolved in 2 ml of pure water and subjected to a nitrogen bubbling for 2 minutes. To this were added 2.9 mM of ammonium persulfate and 5.8 mM of N,N,N',N'-tetramethylethylenediamine to polymerize. After 1 hour, the solution was placed in a semipermeable membrane bag having a fractionation molecular weight of 25,000 and dialyzed against pure water for one day. After that, the solution was freeze-dried to give an aimed polymer.

Example 2

Synthesis of DNA and a Complex

To pQBI 63 (0.1 µg; 0.46 nmol/µl in terms of anionic charge) as DNA was added the polymer synthesized in Example 1 so as to make the charge ratio 0, 0.5, 1.0, 1.5, 2.0, 3.0, 5.0 and 10.0, the total amount was made 10 µl with PBS and the mixture was allowed to stand at room temperature for 30 minutes to give the aimed gene complex.

Each of them was analyzed by gel electrophoresis. The result is shown in FIG. 3.

Example 3

Experiments on Disintegration of the Complex by a Caspase-3 Signal and Release of DNA To pQBI 63 (0.1 µg; 0.46 mmol/µl in terms of anionic charge) as DNA was added the polymer synthesized in Example 1 so as to make the charge ratio 0, 0.5, 1.0, 1.5, 2.0, 3.0, 5.0 and 10.0, 2.0 µl of an assay buffer (50 mM Hepes, 100 mM NaCl, 0.1% CHAPS, 1 mM EDTA, 10% glycerol and 10 mM DTT) were added and the total amount was made 10 µl with sterilized water. After 30 minutes, caspase-3 (2U, 4 µl) was added, incubation was carried out for 30 minutes and analysis was conducted by a gel electrophoresis.

The result is shown in FIG. 4.

Example 4

Production of a Phosphorylation Signal-Responsive Polymer

Production was carried out according to the already-mentioned synthetic method II. Namely, at first, monomer of a substrate peptide type was synthesized and this was subjected to a radical copolymerization with acrylamide to give an aimed product. With regard to the monomer of a substrate peptide type, N-methacryloylalanine was synthesized and then it and other Fmoc amino acid were used to synthesize the monomer by means of a solid phase synthesis using an automatic peptide synthesizer.

(1) Synthesis of N-Methacryloylalanine

Sodium hydroxide (1.24 g) and L-alanine (2.76 g) were dissolved in pure water and, under cooling with ice, a solution where methacryloyl chloride (3 ml) was dissolved in THF (15 ml) and an aqueous solution (17 ml) containing sodium hydroxide (1.21 g) were simultaneously dropped thereinto. After that, the mixture was stirred at room temperature for 4 hours, acidified with 2M hydrochloric acid and extracted with ethyl acetate. The organic phase was dried, concentrated in vacuo, washed with ether and dried in vacuo to give an aimed product. Yield was 1.76 g (36%).

(2) Synthesis of Monomer of a Peptide Type

Each Fmoc-amino acid (0.78 mmol) was taken in a reactor and a peptide was synthesized by an automatic synthesizer. After the reaction, a peptide resin was added to a mixed solution of trifluoroacetic acid (9.5 ml), pure water (0.25 ml) and triisopropylsilane (0.25 ml) and the mixture was allowed to stand for 2 hours and sucked. The resin was washed with trifluoroacetic acid, the washing and the filtrate were combined, ether in a ten-fold amount was added thereto and the peptide separated out therefrom was filtered and dried in vacuo. The crude peptide was purified by a reverse phase HPLC (0.1% aqueous solution of TFA/0.1% TFA-acetonitrile=15%→50% (15 minutes)) whereby 34.4 mg of monomer of a peptide type were prepared.

(3) Synthesis of a Positively-Charged Polymer

Acrylamide (20 mg, 0.28 mmol) was dissolved in 2 ml of pure water and subjected to a nitrogen bubbling for 2 minutes. To this were added ammonium persulfate (1.32 mg, 5.78 µmol) and N,N,N',N'-tetramethylethylenediamine (1.77 µl) to polymerize. After 1 hour, the solution was placed in a semipermeable membrane bag having a fractionation molecular weight of 25,000 and dialyzed against pure water for one day. After that, the solution was freeze-dried to give an aimed polymer.

Example 5

Formation of a Complex of the Polymer With the Gene

With regard to DNA, gene pQBI 63 of a plasmid type encoding a green fluorescent protein was used. To the DNA (0.1 µg; 0.46 nmol/µl in terms of charged amount of anion) was added so as to make the positive charge 0, 0.55, 1.10, 1.65, 2.20, 3.3, 5.5 and 11-fold to the negative charge of the DNA, then 2.0 µl of a buffer for transcription (400 mM Hepes (pH 7.5), 160 mM magnesium chloride, 10 mM spermidine and 200 mM DTT) were added and the total amount was made 10 µl using sterilized water to give an aimed gene complex. Small amount was taken out from each solution and formation of a complex was evaluated by gel electrophoresis. The result is shown in FIG. 6.

Example 6

Phosphorylation of the Polymer in the Complex Using Protein Kinase A

To the above complex solution were added an aqueous solution of ATP (18 mM, 2.3 µl) and a PKA subunit (25 U/µl) followed by being allowed to stand at room temperature for 2 hours. Small amount of each solution was taken out and disintegration of the complex and release of the DNA were evaluated by gel electrophoresis. The result is shown in FIG. 7.

Example 7

Activation of Transcription by Protein Kinase A Signal Using a Complex

To 6.5 µl of an aqueous solution (DNA, 1 µg) of DNA (pQBI 63, coding for GFP; 150 µg/ml) were added 2.5 µl of a mixed solution of amino acids, a solution (10 µl) of S30 Premix without amino acids and 7.5 µl of T7S30 extract, the total volume was made 30.2 µl with a PBS buffer and the product was used as a control. Further, to this solution were added a solution using a complex prepared by addition of the synthesized polymer instead of DNA so as to make the charge ratio 10 and a solution where an ATP solution (45.4 mM, 1.3 µl), an aqueous solution of magnesium chloride (45.4 mM, 1.5 µl) and an active-type protein kinase A (25 U/ml, 1.0 µl) were previously added to the complex and each phosphorylated solution was incubated at 37° C. for 2 hours after addition of S30 Premix, T7 extract for circular system and an amino acid mixture followed by dipping in ice water for 5 minutes. Each solution was diluted to an extent of 250 µl with sterilized water and fluorescence was measured. The result is shown in FIG. 8.

INDUSTRIAL APPLICABILITY

The present invention provides a gene complex forming a strong ion complex with gene and the gene complex of the present invention specifically reacts with a signal response of a cell whereby gene is able to be released. Therefore, the gene complex-forming material of the present invention is characterized by comprising a water-soluble polymer in which a peptide having an amino acid sequence being selectively able to be recognized by a signal-responsive specific enzyme and an amino acid sequence of cationic part being able to form an ion complex with gene is bonded.

By using the gene complex of the present invention, it is able to be transferred into a living body efficiently as a stable gene complex upon transfer and, in a specific target cell, the gene complex is specifically disintegrated to release a gene whereby the gene is able to be efficiently and selectively transferred into the living body.

Further, abnormality of a protease signal has been observed in hepatitis, various inflammatory diseases and many neurodegenerative diseases such as Alzheimer's disease and, in addition, abnormality of activity of kinase forming a phosphorylation signal has been known in various cancers and cardiac diseases. In accordance with the method of the present invention, it is now possible that the signal is captured and gene is transferred into those abnormal cells efficiently, easily and selectively whereby the transferred gene can be activated in the cells. The present invention provides a creation of such an entirely novel pharmaceutical concept.

The invention claimed is:

1. A gene transfer agent, comprising:
a gene complex-forming synthetic material molecule comprising
a water-soluble polymer, and
at least one peptide comprising SEQ ID NO: 2, said at least one peptide being covalently bound to said water-soluble polymer,
wherein a portion of said at least one peptide is cleaved and separated from a remainder of said at least one peptide by the action of a protease, whereby a positive charge of the gene complex-forming synthetic material molecule is removed.

2. A gene transfer agent, comprising:
a gene complex-forming synthetic material molecule comprising
a water-soluble polymer, and
at least one peptide comprising SEQ ID NO: 4, said at least one peptide being covalently bound to said water-soluble polymer,
wherein said at least one peptide is phosphorylated by an action of a phosphorylating enzyme, whereby a positive charge of the gene complex-forming synthetic material molecule is neutralized.

3. A gene complex, comprising:
a gene complex-forming synthetic material molecule comprising
a water-soluble polymer, and
at least one peptide comprising SEQ ID NO: 2, said at least one peptide being covalently bound to said water-soluble polymer, and
a gene bound by ionic binding to said at least one peptide,
wherein a portion of said at least one peptide is cleaved and separated from a remainder of said at least one peptide by the action of a protease, Whereby a positive charge of the gene complex-forming synthetic material molecule is removed, and
wherein upon cleavage of said portion of said at least one peptide, the gene is released into a specified cell, thus activating the gene transferred into the cell.

4. A gene complex, comprising:
a gene complex-forming synthetic material molecule comprising
a water-soluble polymer, and
at least one peptide comprising SEQ ID NO: 4, said at least one peptide being covalently bound to said water-soluble polymer, and
a gene bound by ionic binding to said at least one peptide,
wherein said at least one peptide is phosphorylated by an action of a phosphorylating enzyme, whereby a positive charge of the gene complex-forming synthetic material molecule is neutralized, and
wherein upon neutralization of the positive charge of the gene complex-forming synthetic material molecule, the gene is released into a specified cell, thus activating the gene transferred into the cell.

5. The gene complex of claim 3, wherein the gene is DNA.

6. The gene complex of claim 4, wherein the gene is DNA.

7. The gene transfer agent of claim 1, wherein said protease is caspase-3.

8. The gene complex of claim 3, wherein said protease is caspase-3.

9. The gene transfer agent of claim 2, wherein said phosphorylating enzyme is protein kinase A.

10. The gene complex of claim 4, wherein said phosphorylating enzyme is protein kinase A.

11. The gene transfer agent of claim 1, wherein the water-soluble polymer comprises acrylic acid and/or methacrylic acid.

12. The gene complex of claim 3, wherein the water-soluble polymer comprises acrylic acid and/or methacrylic acid.

13. The gene transfer agent of claim 2, wherein the water-soluble polymer comprises acrylic acid and/or methacrylic acid.

14. The gene complex of claim 4, wherein the water-soluble polymer comprises acrylic acid and/or methacrylic acid.

15. The gene transfer agent of claim 2, wherein said at least one peptide consists of SEQ ID NO: 4.

16. The gene complex of claim 4, wherein said at least one peptide consists of SEQ ID NO: 4.

17. The gene transfer agent of claim 1,
wherein said gene complex-forming synthetic material molecule comprises a plurality of peptides each comprising SEQ ID NO: 2, each of said plurality of peptides being covalently bound to said water-soluble polymer, and
wherein a portion of each of said plurality of peptides is cleaved and separated from a remainder of a corresponding one of said plurality of peptides by the action of said protease, whereby a positive charge of the gene complex-forming synthetic material molecule is removed.

18. The gene transfer agent of claim 2,
wherein said gene complex-forming synthetic material molecule comprises a plurality of peptides each comprising SEQ ID NO: 4, each of said plurality of peptides being covalently bound to said water-soluble polymer, and
wherein each of said plurality of peptides is phosphorylated by an action of said phosphorylating enzyme, whereby a positive charge of the gene complex-forming synthetic material molecule is neutralized.

19. The gene complex of claim 3,
wherein said gene complex-forming synthetic material molecule comprises a plurality of peptides each comprising SEQ ID NO: 2, each of said plurality of peptides being covalently bound to said water-soluble polymer, and
wherein a portion of each of said plurality of peptides is cleaved and separated from a remainder of a corresponding one of said plurality of peptides by the action of said protease, whereby a positive charge of the gene complex-forming synthetic material molecule is removed.

20. The gene complex of claim 4,
wherein said gene complex-forming synthetic material molecule comprises a plurality of peptides each comprising SEQ ID NO: 4, each of said plurality of peptides being covalently bound to said water-soluble polymer, and
wherein each of said plurality of peptides is phosphorylated by an action of said phosphorylating enzyme, whereby a positive charge of the gene complex-forming synthetic material molecule is neutralized.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Chemically synthesized

<400> SEQUENCE: 1

Ala Gly Asp Glu Val Asp Gly Lys Lys Lys Lys Lys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: UNSURE
<222> LOCATION: (1)...(2)...(7)
<223> OTHER INFORMATION: Any amino acid

<400> SEQUENCE: 2

Xaa Xaa Asp Glu Val Asp Xaa Lys Lys Lys
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (8)
<223> OTHER INFORMATION: AMIDATION

<400> SEQUENCE: 3

Ala Leu Arg Arg Ala Ser Leu Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Chemically synthesized
<220> FEATURE:
<221> NAME/KEY: UNSURE
<222> LOCATION: (1)...(5)...(8)
<223> OTHER INFORMATION: Any amino acid

<400> SEQUENCE: 4

Xaa Leu Arg Arg Xaa Ser Leu Xaa
1               5
```